United States Patent [19] [11] Patent Number: 5,362,653
Carr et al. [45] Date of Patent: Nov. 8, 1994

| [54] | EXAMINATION OF OBJECTS OF MACROMOLECULAR SIZE |
|---|---|
| [76] | Inventors: Robert J. G. Carr, Wayside, Thorneydown Road, Winterbourne Gunner, Salisbury SP4 6LN; David J. Clarke, Carefree Rivermead Idmiston, Salisbury, Wilts; Anthony Atkinson, Twingley Winterbourne Gunner, Salisbury SP4 6JJ, all of United Kingdom |
| [21] | Appl. No.: 842,130 |
| [22] | PCT Filed: Sep. 12, 1990 |
| [86] | PCT No.: PCT/GB90/01407 |
|  | § 371 Date: May 6, 1992 |
|  | § 102(e) Date: May 6, 1992 |
| [87] | PCT Pub. No.: WO91/04507 |
|  | PCT Pub. Date: Apr. 4, 1991 |
| [30] | Foreign Application Priority Data |
|  | Sep. 12, 1989 [GB] United Kingdom ............... 8920571 |
| [51] | Int. Cl.⁵ .................. G01N 21/17; G01N 29/00 |
| [52] | U.S. Cl. .................. 436/165; 324/71.1; 324/71.4; 356/441; 356/442; 356/335; 356/311; 422/73; 422/82.05; 422/82.11; 436/149 |
| [58] | Field of Search ............... 422/73, 82.01, 82.05, 82.06, 82.07, 82.11; 356/441, 442, 335, 336, 337, 311; 377/10; 324/71.1, 71.4, 713; 436/149, 165 |

[56] References Cited

U.S. PATENT DOCUMENTS

| 4,420,720 | 12/1983 | Newton et al. ............... 324/71.1 |
| 4,760,328 | 7/1988 | Groves ............... 324/71.4 |
| 4,778,657 | 10/1988 | Spohr ............... 324/71.4 |

FOREIGN PATENT DOCUMENTS

| 0296262 | 12/1988 | European Pat. Off. . |
| 0308537 | 3/1989 | European Pat. Off. . |

OTHER PUBLICATIONS

Fischer, J. Vac. Sci. Technol. B 3(1), Jan./Feb. 1985, pp. 386–390.
Durig, et al., IBM J. Res. Develop., vol. 30 No. 5, Sep. 1986, pp. 478–483.
Fischer, et al, Appl. Phys. Lett., 52(4), 25 Jan. 1988, pp. 249–250.

Primary Examiner—Jill A. Johnston
Attorney, Agent, or Firm—James B. Middleton

[57] ABSTRACT

In a method and apparatus for examining samples comprising individual objects (28) of macromolecular or similar size, or smaller, an instrument element (14) comprises a substrate (16) overlaid with a thin film layer (18) of a material that is electrically conductive and/or at last partly optically opaque. A discontinuity comprising an aperture (26) or an asperity is formed in or on the element (14) in a known location, and the sample (28) is brought to this discontinuity so that it is not necessary to search for the sample by scanning. Energy (e.g. electrical energy or light) is applied to the element (14) and, with the latter and the sample in intimate association, e.g. with the sample inside the aperture (26), changes in the radiation from the sample site resulting from the presence of the sample are detected.

9 Claims, 3 Drawing Sheets

EXAMINATION OF OBJECTS OF MACROMOLECULAR SIZE

This invention relates to methods and apparatus for examining individual objects the size of which is of the general order of magnitude of macromolecules and their aggregates, or smaller. These objects may consist of particles, or of other materials or structures of generally similar dimensions. Where they are particles, they may in fact actually be macromolecules, for example enzymes or other proteins, or biological macromolecules or other larger structures such as viruses. The field covered by the invention does not however exclude the examination of particles of generally submicron size. Objects for examination, or being examined, will sometimes herein be called "samples", for convenience.

Current techniques, such as scanning tunnelling microscopy, atomic force microscopy and scanning near field optical microscopy, are already well known, and have considerably lowered the limit of molecular resolution that is now possible. In all these techniques, the image is built up from a scanned signal which is generated by interaction of the structure of the sample particle with a probe tip having dimensions comparable with that of the sample.

In scanning tunnelling microscopy (STM) an ultra-fine, chemically etched electrode is brought very close to the sample, so that electrons can pass by quantum tunnelling across the free space between the electrode tip, or part thereof, and the surface of the sample. The samples are mounted on a conductive substrate, and the probe is scanned across the substrate in order to find a sample for examination. Piezoelectric transducers are used to control the movement of the probe. One disadvantage of STM is that the sample must be sufficiently electrically conductive, and with many types of particle, particularly biological particles, this requires pretreatment of the sample macromolecule in order to improve its conductivity. This has been achieved by using metal shadowing or doping with conductive salt ions; such treatment can however alter the characteristics of the sample, so that in some cases it becomes self-defeating.

Another, somewhat similar, device is the scanning capacitance microscope, which measures the capacitive, changes associated with sample structures but on a much lower resolution. It can operate to the same order of magnitude of sample size as conventional optical microscopy, or larger.

In atomic force microscopy (AFM), an ultra-fine, very lightly spring loaded probe tip is scanned across an area containing a sample, and then across the sample itself. The movement of the tip as it is deflected by repulsion between the Van der Waals forces between the tip and the sample is monitored so as to generate a topographical image of the surface of the sample. A major disadvantage of AFM is that with most biological macromolecular structures, particularly in solution, the forces generated by the probe tip will tend to damage or destroy the sample. The AFM technique is therefore somewhat limited in scope, and, as is also generally true of STM, it is really only suitable for use where the sample can be shadowed, i.e. coated, with metal.

Electromagnetic radiation can be greatly amplified when interacting with strongly curved parts of a surface due to quasi-static concentration of field lines (the so-called "lightning rod" effect). This effect is responsible for the development of surface-enhanced Raman scattering or roughness-induced electrical breakdown. It is also responsible for the strong elastic light scattering associated with microscopic holes in a film (apertures) or protrusions (asperities) from a surface, a process closely related to Mie scattering from small spheres which act as "short optical antennae" (SOA). The degree of scattering from these SOA is related to their size (curvature) and dielectric properties.

The method employed in a scanning near field optical microscope (SNOM) is a variant on the STM technique, and is essentially optical in character. The SNOM includes a component which serves as an optical source of suitably small dimensions and which performs an active function in the examination process. Such a component will be found in what will be generally called an "instrument element" in this description. In the SNOM, the instrument element can comprise a substrate of a suitable waveguide material, having a very thin layer of gold deposited on one surface. The gold is so applied that it has small apertures or asperities (generally no larger than 100 nm), which act as centres for light scattering. In other words, the apertures or asperities act as short optical antennae. The effect of this scattering is that some radiation leaks from the apertures or asperities in the gold film, the intensity of the scattered radiation being dependent on the size of the aperture and on the dielectric properties of the materials. The scattered light emanating from the apertures or asperities is easy to detect using conventional optics. The SNOM carries out optical topographical imaging of samples by monitoring the changes in intensity of the light scattered from the aperture or asperity as the sample is brought into very close proximity to the radiating near field emanating from the aperture or asperity. In the near field region, the electric field of the radiation is severely damped by the approaching sample, and this sensitivity is used for the topographical imaging of the sample.

A major drawback in all of these known methods is that before a sample can be examined, it must first be found. Thus, a region of the sample preparation which contains an object of interest must first be identified, and this can be difficult. Although attempts have been made, in connection with both STM and AFM, to associate these types of microscope with electron microscopes or conventional optical microscopes, for example, in order to take advantage of the wider range of scan of these more conventional instruments, searching for a suitable specimen can still waste a very large amount of time, because STM, AFM and SNOM inherently have a small width of scan. SNOM also requires the mounted sample to be positively approached towards an aperture or asperity in the gold film. As also with STM and AFM techniques, the mounting or immobilising of the sample in SNOM can result in damage to the sample. At the same time it is not possible to bring the optical probe close enough to the sample to be at an optimum distance from it without risking untoward close contact, or even impact, between the sample and the probe. Even so, the distance between the sample and the aperture has to be very closely controlled, and as with the other techniques, the equipment involved is somewhat complex and expensive.

Another disadvantage found with the current techniques is that, whereas resolution normal to the plane of the aperture in the instrument element defining the site at which examination of the sample is to take place (vertical resolution) is high, lateral resolution is much lower. In the case of STM and AFM instruments, it is not possible to produce a probe tip narrow enough to produce lateral resolution comparable to the high degree of vertical resolution which is possible. This drawback is more marked in the case of the SNOM, and the smallest probe diameter is of the order of 30 nm. A further disadvantage is that interaction between the sample particles and the radiation scattered at the aperture may of necessity be relatively poor.

Another method of detecting individual cells (1-5 μm and larger) is that of conventional flow cytometry, in which cells are hydrodynamically caused to pass through an optical scattering volume (laser beam) for analysis. As with other conventional optical systems, the resolution available with flow cytometry is limited by diffraction effects, which limit the degree of beam focussing that can be obtained.

According to one aspect of the invention, a method of examining sampling comprising individual objects of macromolecular size or smaller being a non-scanning, non-image-forming method, from which measurement of distances is absent and which comprises the steps of:

(i) bringing a sample into proximity with an instrument element comprising at least one thin film layer having a discontinuity in a known or identifiable location;

(ii) exciting the instrument element with electromagnetic radiation to which the material of said layer is substantially opaque, so as to cause a detectable signal to emanate from the discontinuity;

(iii) causing the sample to move into intimate association with the discontinuity so that the sample and the discontinuity then interact with each other to produce changes in said detectable signal; and (iv) continuing to excite the instrument element with said radiation while detecting said changes.

Where the discontinuity is an aperture formed through the film layer, the "intimate association" referred to above consists in the presence of the sample, or part of the sample, in the aperture itself. Accordingly, samples suitable for examination with this arrangement will generally consist of particles and other bodies which can be brought into the aperture. The aperture is preferably larger than at least one expected dimension of the sample, but of a similar order of magnitude. However, the arrangement can also be used for study of the interaction between two samples, one of which may for example be partly in the aperture and the other one close to it.

If the discontinuity is an asperity projecting from the film layer, the sample may or may not be of such a configuration that it could be mounted in or pass through an aperture. Use of asperities is especially suitable where the sample consists of a membrane or analogous structure. The "intimate association" can take any suitable form, depending on requirements: the sample may for example be in actual contact with the asperity, or almost in contact with it. In one type of practical embodiment, the portion of the film layer bearing the asperity can be coated with a sample membrane, with other samples, of any kind, then being brought into intimate contact with the latter at the asperity so that these samples can be analysed in terms of their interaction with the membrane by detection of the changes in radiation emanating from the asperity in the presence of such a sample.

In general, the instrument element with its discontinuity is preferably, though not necessarily, arranged in a fixed position, so that the relative movement between sample and discontinuity preferably consists in conveying or attracting the sample towards the discontinuity and into the appropriate intimate association with it, using electrophoresis or any other suitable means.

Preferably, the method also includes the further step of applying an energy field or fields to the discontinuity in such a way as to modulate or modify the behaviour and/or the structure of the sample. This additional or modulating energy may or may not be of the same kind as the basic energy which is applied to cause the detectable signal to occur at the discontinuity in the first place. This basic applied energy may be electrical energy or electromagnetic energy such as light. In the latter case, the aperture or asperity acts as a short optical antenna.

The invention, in a second aspect, is directed to apparatus for performing the method of the invention, said apparatus comprising an instrument element that comprises at least one thin film layer, having a discontinuity in a known or identifiable location; means for causing relative movement between a sample and the discontinuity and for bringing them into intimate association with each other; means for exciting the instrument element with electromagnetic radiation to which the material of said layer is substantially opaque, so as to cause a detectable signal to occur at the discontinuity; and detecting means for detecting said signal and changes therein, without scanning or image forming, the apparatus defining means connecting the discontinuity with the detecting means whereby the latter can receive said signal.

Considering the case where the discontinuity is an aperture, it is an important feature of the invention that the sample is actually brought into close proximity to, or preferably actually into the interior of the aperture itself. Thus, instead of examination of a sample being possible only when it lies in the near field region outside an aperture, into which radiation is scattered from the latter, as in conventional SNOM practice, the sample can actually be brought into the intimate association, discussed above, with the aperture as well as the near field. The invention thus enables advantage to be taken of tunnelling effects in addition to the near field optical effects which characterise known methods based on scanning. Thus the detectable signal may take more than one form, e.g. changes in electromagnetic radiation or electrical parameters at the discontinuity (collectively referred to below as "radiation" for convenience).

The net result is that the sensitivity of the apparatus is greatly increased, since the radiation field within the aperture, of a similar order of physical size to the particle, will have a profound effect on the behaviour of the radiation, and therefore a substantially increased effect on the radiation which "leaks" from the aperture. These changes can be quite readily detected by conventional means. Similar considerations apply where the discontinuity is an asperity.

In alternative embodiments, in which light is used as the source of energy, the film layer is then made at least partly opaque to light, the substrate being able, either by being porous or otherwise, to transmit light, so that light applied through the substrate leaks from it through the aperture in the film layer. In this case, as indicated above, the presence of the particle within the aperture itself will cause a considerably more marked disturbance of the light leaking from the aperture. Indeed, in this case conventional optical equipment will in most cases be sufficient to detect the changes in the visible light caused by the presence of the particle in the aperture.

The invention is particularly well adapted for the examination of samples in solution. An electrical potential is applied across the instrument aperture so that the solution, containing the sample in free solution in a solvent, migrates towards it, for example by electrophoresis, and particles or other samples in solution can thus themselves migrate to the location of the aperture and so into the latter. For this purpose, the substrate is porous and its electrical conductivity is low enough, i.e. it is a sufficiently good insulator, for the aperture and porous channel to act as a preferred leakage path.

The invention eliminates the need to scan a surface over which sample objects are attached, firstly in order to find a sample for examination in the first place, and secondly to examine the sample once it has been found. Instead, the sample is deliberately directed into a single predetermined location, where it is then examined. It follows that a plural number of samples can be simultaneously examined, using their separate interactions with a corresponding number of apertures and/or asperities.

Where this predetermined location consists of an aperture in or through the instrument element itself, the sample is examined by observing the interaction between the applied energy and the sample inside the aperture (or that part of it that is inside the aperture as the particle electrophoreses through the latter). The aperture is preferably of known dimensions, so that the detection volume (i.e. the volume of the aperture) is highly specific and suitable for the size and associated field of a sample passing through it. This results in a substantial reduction in unwanted "noise", and hence a very significant improvement in signal-to-noise ratio, resulting in turn in a substantial improvement in resolution and accuracy of the usable output signals. These improvements are also evident where the discontinuity is an asperity. The invention also offers other advantages, some of which have already been mentioned above.

The invention is intended primarily for use on samples in which the interaction between the sample and the applied energy, e.g. light, is governed by quantum mechanics. It should however be understood that the invention is also applicable to the examination of microscopic objects large enough for more conventional laws to be applied. Many viruses for example, larger than about 30 nm in size, fall into this category.

Analysis of the object (i.e. particle, molecule or structure, as discussed earlier in this specification) in the aperture can be carried out using time-resolved optical techniques (fluorescence), or any other analytical method operating in the time domain, and in which the object is specifically modulated, optically or electrically, so as to be optically or electrically phase locked into any given detection principle.

A few examples of the application of the invention will now be described, by way of example only, with reference to the accompanying drawings, all of which are highly diagrammatic and not to scale. In the drawings.

Figure 1:
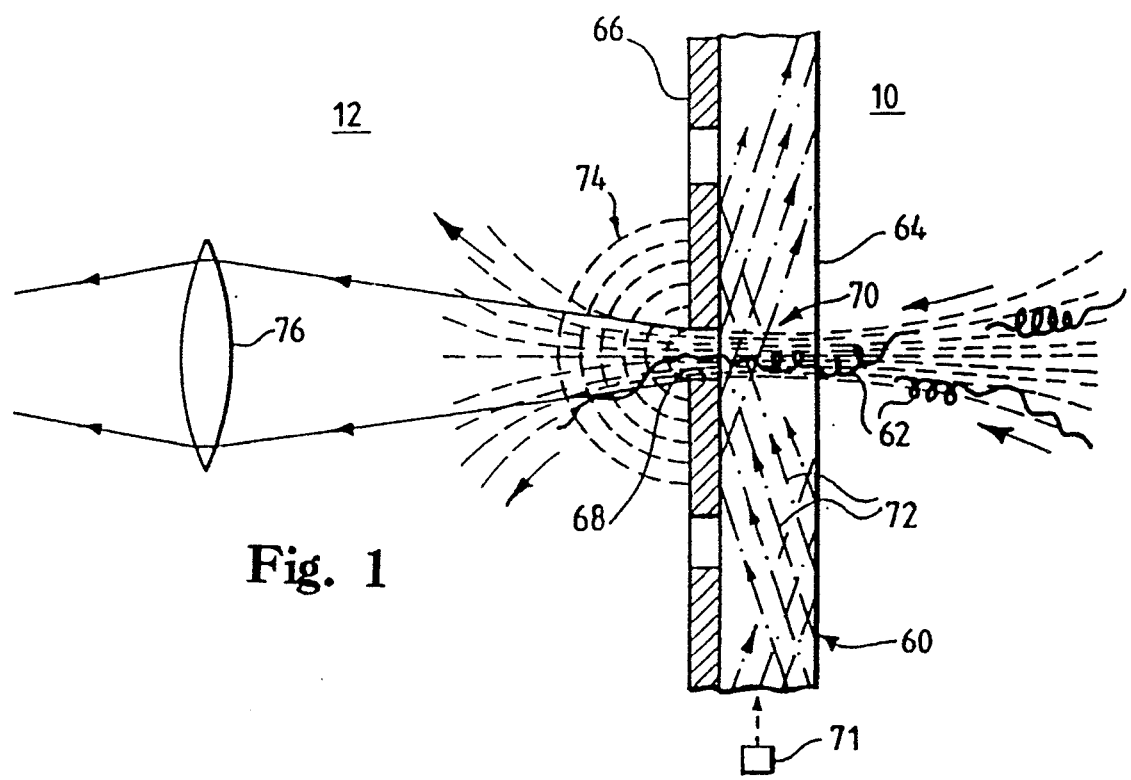
FIG. 1 shows in cross section part of the instrument element of one form of apparatus according to the invention, in which particles are caused to migrate through the instrument element at a known location, and are examined by observing the interaction between them and applied light.
Figure 2:
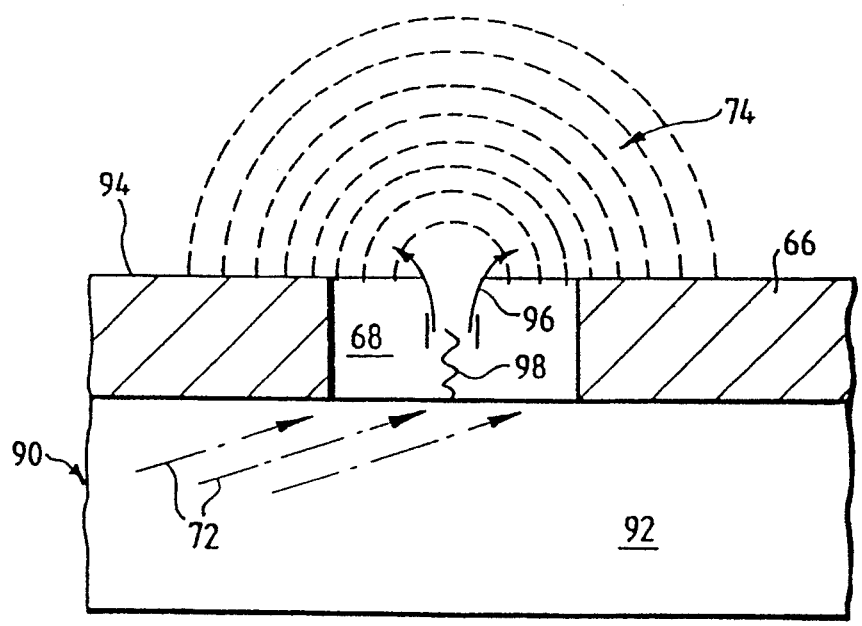
FIG. 2 is a cross section through part of the instrument element in which the particle is held stationary in the aperture.
Figure 3:
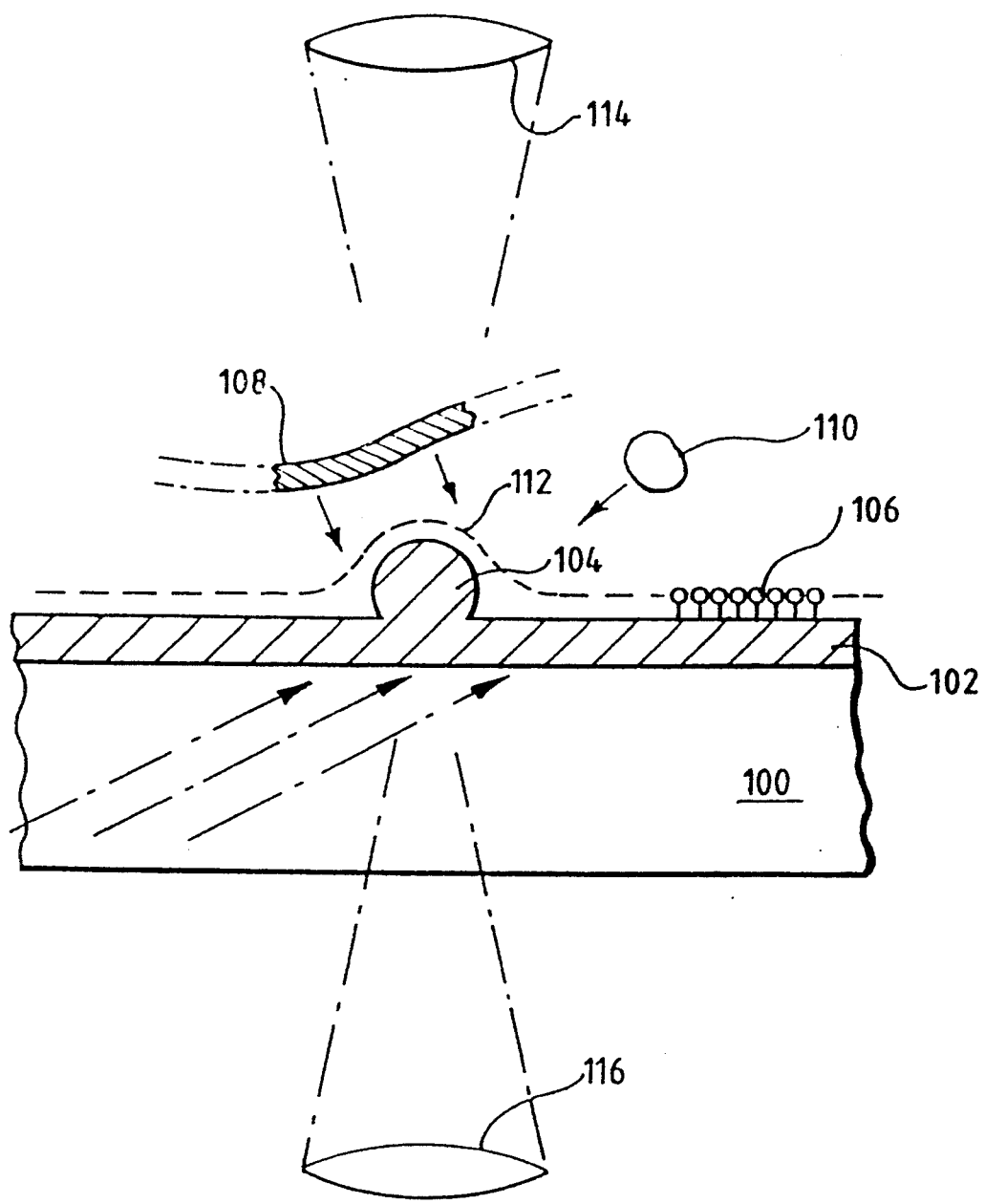
FIG. 3 illustrates one use of the invention where the discontinuity is an asperity acting as a short optical antenna.

The applied energy used in the method and apparatus of the invention is any form of electromagnetic radiation, and in FIGS. 1 to 3 this electromagnetic energy is light. In FIG. 1, an instrument element 60 separates from each other two receptacles 10 and 12. The receptacle 10 contains a solution, typically an aqueous solution (though any suitable solvent, liquid or gaseous, can be used), in which particles 62 to be examined are in free solution, in the solvent. The element 60 comprises a porous, translucent, electrically insulating substrate membrane 66, on the front face of which an opaque film layer 66 is deposited by any suitable means. The layer 66, which may typically be of metallic gold, may have any suitable thickness, typically of the order of 20 nm. At least one hole 68 is formed, by any known method, through the film layer 66, at a known location in the latter. The hole 68 and the porosity of the membrane 64 immediately behind it together define what is referred to herein as an "aperture", or path, through the element 60. This aperture is indicated at 70 in FIG. 1.

If desired, the instrument element may have a number of such apertures, all in known locations but of different sizes so that the apparatus can effectively handle a variety of different kinds of particles of different sizes.

A voltage is applied between the two receptacles 10 and 12, such as to cause the solution to migrate electrophoretically from the former towards the later through the hole 68.

It will of course be understood that close interaction between the particle and the aperture may be obtained by any suitable technique using a selective physical or chemical motive force. Examples include osmosis, diffusion and centrifugation. The preceding examples, the solution is thus caused to migrate electrophoretically in the receptacle 10 to the instrument element 60, so that the particles 62 pass through the aperture in the latter.

The translucent membrane 64, which is preferably transparent, is edge illuminated, for example by means of a laser 71, at an angle of incidence such that it acts as a waveguide, as indicated by the directional lines 72 which represent light paths within the membrane-substrate layer. Although the light following the paths 72 is generally constrained within the membrane 66, some of it will leak outwardly through the hole 68 to give near-field light leakage or scattering as indicated at 74. The light paths 72 are at grazing incidences only, so that light does not penetrate the film layer 66, except at the holes 68 which act as the scattering centres.

As a particle 62 approaches the aperture or porous path 70 under electromotive force, it will start to interact with the electromagnetic field associated with the aperture which acts as a short optical antenna (SOA) according to the well-known principles explained above. The effect of this is that the scattered light 74 will change in respect of at least one optical parameter, such as intensity, polarisation, phase, spectral content or fluorescence. This effect will increase as the particle approaches the hole 68, and be strongest when the particle is actually in that hole. The scattered radiation 74, modified by the particle, therefore represents an output signal which can be received by any suitable optical receptor. In this example, the latter is a conventional microscope objective lens 76, typically of ×40 magnification.

The optical signal from the objective lens 76 may then be processed and analysed by any suitable optical and/or electro-optical instrumentation, not shown.

It should be noted that this process again involves interaction between the light itself, i.e. the electromagnetic field associated with the aperture 68, acting as an SOA, and the electrostatic or dielectric characteristics of the particle. Accordingly, the porosity of the membrane 64, and, once again, the size of the hole 68, are chosen to take into account the electrostatic double layer surrounding the particle and forming, in electrostatic terms, part of the particle itself. The hole 68 is typically from 20 to 200 nm in diameter. We shall return later herein briefly to the significance of this double layer.

The opaque layer 66 may be made unsupported, being back-illuminated at suitable grazing incidence angles such that light does not pass directly through the hole 68 but only escapes from it by virtue of small aperture/asperity scattering effects. However, where the layer 66 is supported by a substrate 64, the latter may be of any suitable material which is porous to the macromolecule, for example hydrophilic or hydrophobic gel, compatible with the solvent in which the particles 62 are carried in free solution. Another possible material for the membrane is controlled-pore glass. The objective 76 is focussed on one particular selected hole 68, and the film layer 66 may be formed with no other perforations. It may however have a large number of perforations, and FIG. 1 shows more than one. Particles passing through any of these other perforations are of no account. Alternatively, of course, perforations of different sizes, each in a known location onto which the objective 76 can be focussed beforehand, may be provided for the examination of particles of different sizes.

Reference is now made to FIG. 2, in which the instrument element, 90, does not define a path for a particle through the element itself. Here the aperture consists merely of the hole 68 formed in a film layer 66, generally similar to that described with reference to FIG. 1 and mounted on a transparent waveguiding substrate layer 92, which need not be porous but may merely consist of optical glass. The substrate layer 92 is again edge illuminated at grazing incidence, so that the only light passing out through the hole is the leakage radiation 74. The glass substrate 90 is suitably treated by any conventional method for activating it, for example (where it is of glass) by an immobilisation technique such as silanisation such as to enable the samples, for example biological macromolecules, to be simply attached to the glass. Thus, with the substrate 92 of glass and the opaque layer 66 of gold, if the resulting element 90 is treated by a liquid or vapour phase silanisation technique, since gold reacts poorly to such immobilisation chemistries, the element 90 will be activated substantially only on the parts of the glass surface exposed within the hole or holes 68. The sample macromolecules, 96 in FIG. 2, will therefore tend to become attached, by a silane immobilising ligand 98, within the holes themselves. Thus, as before, a signal receptor such as the objective 76 in FIG. 1 can be focussed on one particular hole 68, the particles adhering anywhere else on the element 90 being of no account. Because particles will preferentially attach themselves in holes 68, it is merely necessary to focus on to one of the latter, without the need for any scanning to locate a particle for examination. In this connection, it should be noted that even if some attachment of particles to the gold surface does occur, these will cause no interference since the useful output signals are generated only by structures associated with the hole 68.

When a particle is trapped in a specific location in this way, experiments can be carried out for a number of different purposes on the stationary particle at leisure. In particular, the arrangement shown in FIG. 2 may be used for the detection and analysis of other bodies interacting with the sample or samples located in the aperture 68. It follows that a sample, such as a particle, in the aperture 68 can be augmented with another material, or composite, of suitably small size, which may interact with the sample in such a way as to cause changes to take place in its optical and/or electrical properties. These changes can then be detected and analysed.

FIG. 3 illustrates another embodiment in which the effects of interaction can be studied. In this case the transparent substrate, 100, again has a thin gold film, 102, on one of its surfaces, but here the discontinuity is an asperity instead of an aperture. The asperity is a projection 104 on the outer side of the film 102, which is coated with a layer of a sample material, such as a biological membrane 106, with this layer covering the asperity 104. Other samples, such as a membrane 108 or a particle 110, are brought by electrophoresis or otherwise into contact with, or very close proximity to, the membrane 106 in the region 112 where the latter overlies the asperity 104, such that in this region there is interaction between the transported sample 108 or 110 and the membrane 106.

Light is applied to the instrument element 100, 102, for example via the substrate 100 as already described in connection with FIGS. 1 and 2. The film 102 is thin enough to be only partly opaque to this light so that some light passes through it, the remainder of the light being reflected by the film. The asperity 104 acts as a short optical antenna, causing scattering of both transmitted and reflected light.

When interaction occurs between a sample 108 or 110 and the biological membrane 106, the resulting changes in the light emanating from the SOA asperity 104 can be detected. This may be done, for example, using a transmitted-light lens 114 on the same side of the instrument element as the asperity, or a reflected-light lens 116 on the other side of the element, since both the transmitted and reflected light will be affected by the interaction between the samples.

The configuration of the asperity 104, and its dimensions, can be chosen to suit the particular application for which it is to be used.

Figure 7:
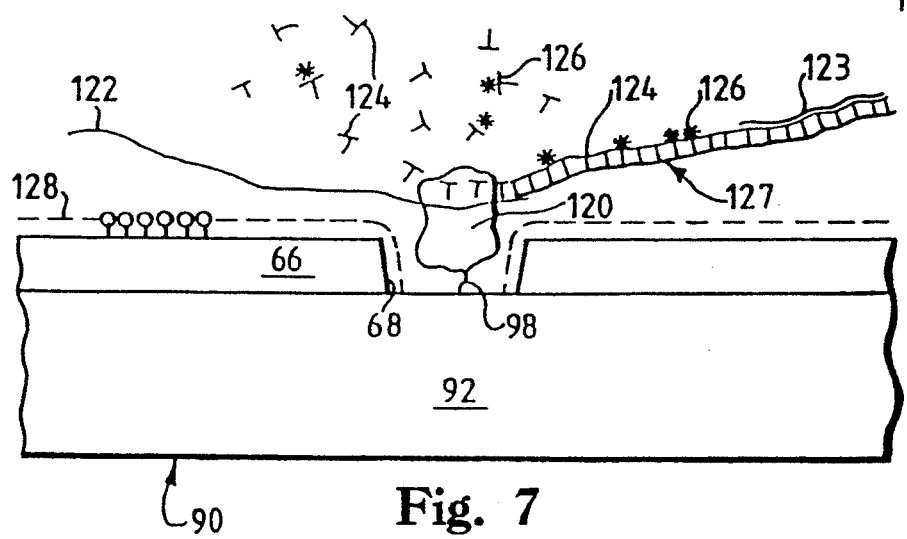
FIG. 7 illustrates a use of the apparatus in DNA sequencing analysis.

Another example, using the instrument element 90 of FIG. 2, is illustrated in FIG. 7. It should be noted that the arrangement seen in FIG. 3 could, however, be used instead. In FIG. 7, a polymerase molecule 120 is attached by a ligand 98 in the aperture 68 over the waveguide substrate 92. A single-stranded DNA molecule 122, with a primer sequence 124 base-paired on to it in a known manner to initiate polymerisation, is brought to the polymerase 120. The progress of the resulting polymerisation with nucleotide bases 124 and fluorescently-labelled bases 126, giving the duplex DNA structure 127, can then be observed and analysed due to the changes in the light emanating from the aperture 68, light being supplied to the substrate 92 as before.

A chemical or biochemical passivation or modification layer 128, of suitable composition, may be applied over the outer surface of the metal layer 66 in order to improve the specificity of binding of the target DNA molecule 122, and/or to reduce non-specific binding. It should be noted that such a layer 128 can be employed in all variants of the method or apparatus of this invention where these effects may be required.

The instrument element can be configured in a miniature waveguide form, e.g. as a slab or other waveguide, or in a fibre optic form. In the latter case it is, for example, capable of being used as a remote, multiplexable fibre optic sensor which can be incorporated, if required, into a network.

Figure 5:
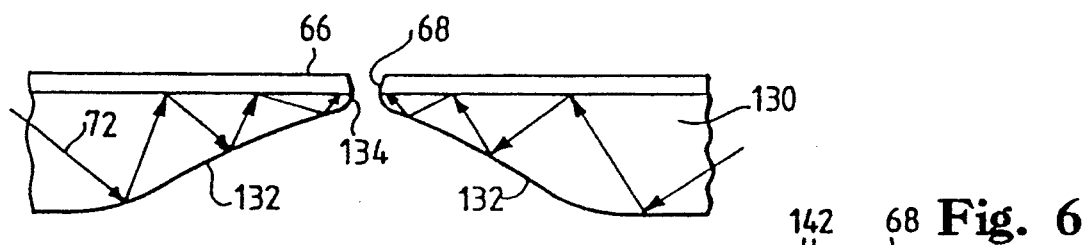
FIG. 5 is a cross section of part of an instrument element incorporating a convergent waveguide.

FIG. 5 shows one example in which the substrate 130 of the instrument element, having a metal film layer 66 and an aperture 68 as before, is of glass so as to act as a monomode optical waveguide. A convergent surface profile 132 is formed on the rear face of the substrate 130 leading to the aperture 68. This profile acts as an efficient, tapered, local waveguide, enhancing containment of the incident light and concentrating the latter at the aperture 68 while reducing interfacial losses.

The convergent profile 132 terminates in a hole 134 aligned with the hole 68 in the layer 66 so that the aperture 68 itself comprises these two holes, which are preferably drilled by high-energy electron beam lithography after suitable masking (a hole-forming technique which can be used for any of the apertures in the various embodiments of the invention in which the discontinuity serving as the working site is an aperture).

The concentration of light at the aperture, together with the reduced losses, may produce flare effects involving sub-wavelength tunnelling effects which can enhance the observable changes that supply the information required when a sample is present at the aperture.

The profile 132 can be of any desired shape, e.g. spherical or conical, and may be formed by etching.

Figure 6:
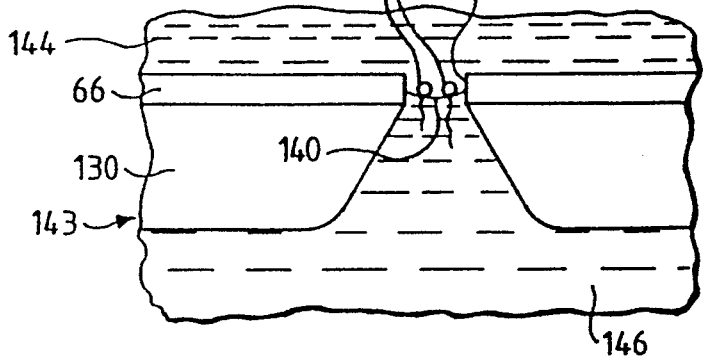
FIG. 6 illustrates a use of the apparatus for studies at a liquid-liquid interface.

Another possible use of apparatus according to the invention is in the study of a stable liquid/liquid interface 140, FIG. 6, or in the study of the behaviour of molecular objects at such an interface. FIG. 10 shows two such molecules, 142, suspended at the interface within the aperture 68 of an instrument element 143 which (in this example) happens to be similar to that shown in FIG. 5, but which need not have a tapered waveguide section. A first liquid solvent 144 is above the element 143, and a second liquid solvent 146 below it. These solvents will be chosen at least partly so that their physical characteristics permit the stable interface 140 to form in the aperture 68. They, and/or the samples, will also be chosen so that the latter are ormphiphilic.

Figure 4:
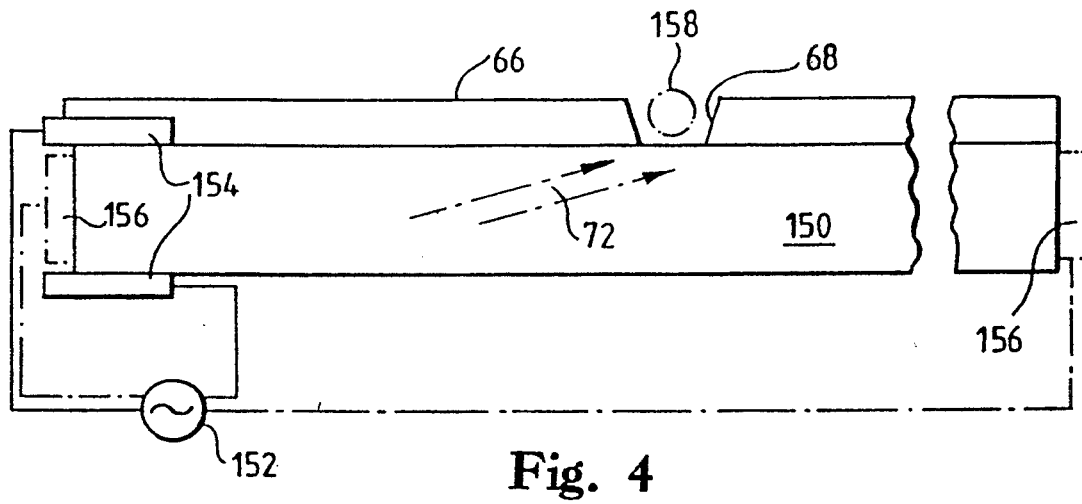
FIG. 4 illustrates the use of piezoelectric effects to produce an applied energy field.

Referring now to FIG. 4, an applied energy field can be created piezoelectrically. In FIG. 4, the substrate 150 of the instrument element is of an optically-transparent piezoelectric material to which a pair of electrodes is fitted, the electrodes being connected through a piezoelectric resonator circuit or driver 152. Depending on the piezoelectric polarity, these electrodes are mounted so as to transmit impulses through the substrate 150 either transversely (electrodes 154) or longitudinally (electrodes 156 in phantom lines). In the former case the whole of the metal layer 66 may serve as an electrode.

With a sample 158 mounted in the aperture 68 in the layer 66, light 72 is transmitted through the substrate as described with reference to FIGS. 1 and 2. In addition, the driver 152 is energised so as to superimpose piezoelectric energy on the substrate, at a frequency which excites the sample at an acoustic (audio or ultrasonic) frequency and modulates the observed optical output. This produces the well-known phenomenon of Brillouin scattering, which depends on the interaction of the applied light and acoustic energy and also on the characteristics of the sample which determine the optical output. Data on such characteristics can in this way be obtained.

The electrostatic double layer of a macromolecular particle has been mentioned above. This is part of its characteristic electrostatic field. In the case of certain biological macromolecules, small differences in primary structure lead to significant differences in their function. Current theories on protein, enzyme and other macromolecule structure and function suggest that secondary and tertiary structure is responsible for generating large electrostatic fields, which may extend to the equivalent of several diameters of the molecule itself. This is true for example in the case of some proteins, especially enzymes. Theoretical studies of these electrostatic fields have indicated a role in the capture of specific substrate molecules at relatively great distances by an enzyme macromolecule. The fields are generally toroidal in shape, and it has been shown that they have their poles centred on the active site of the enzyme, and that they act not only to facilitate interaction between the active site and the substrate molecule, but also align the substrates on their approach to the active sites. The structure and shape of these fields are accordingly likely to be highly characteristic of a specific enzyme, and the present invention provides a useful and versatile method of studying and exploiting these characteristic electrostatic fields in detail.

It should be noted that the invention is not confined to the case where the samples are in solution. Where they are, however, the solvent need not be water or even liquid, but the solution may take any form known to physical chemistry in which the sample particles can be caused to migrate to the examination site, either electrophoretically or under any other selective physical or chemical motive force. One example of such a solution is a gel.

Where the energy used for observation is light, i.e. in optical embodiments, a number of different optical parameters may be studied at the aperture or asperity, notably Brillouin scattering (already mentioned), intensity, fluorescence, polarisation and absorption. The intensity of light scattered at the aperture or asperity (the discontinuity) is modulated by the mass or dielectric of analyte samples in the vicinity of the discontinuity if the latter acts as a scatterer. As to fluorescence, aspects of this that are available for study include intensity of fluorescence, shifts in excitation or emission wavelengths or profiles, decay patterns of fluorescence, and Raman scattering. Fluorescence may be observed by conventional spectroscopy using the apparatus of the invention.

Where a sample is optically active, changes in their polarisation may be detected, including depolarisation.

Absorption of light by a sample can manifest itself in the form of changes in intensity of the incident light, and can cause local heating around the sample (e.g. a molecule), so changing the local optical environment, which may then be analysed, for example by a photothermal technique. Again, absorption may be studied using conventional spectroscopy using the apparatus of the invention.

The thin film, which in the examples given above is of gold, can in practice be of any material that is suitable in terms of electrical conductivity and/or opacity, and which may or may not be a noble metal.

Besides the embodiments of the method and apparatus described above, the invention can be employed in a variety of other configurations and for a variety of other purposes, involving simple examination and analysis of samples; modification of the behaviour and structure of individual samples with examination and analysis of such modifications and/or their effects; and study of the interaction between a plurality of samples and/or between one or more samples and their environment.

Whatever embodiment of the invention is employed, and for whatever purpose, it will be seen that, since the need for scanning to find a sample is avoided, and since consequently the examination site can be predetermined in advance, it is also possible to calibrate that site in conjunction with the parts of the apparatus that receive the signals and analyse them to give information about the sample. This will tend greatly to decrease the possibility of inadvertent error, such as may occur when the location of the site is randomly determined only by the fact that a sample happens to have settled there.

It should however be noted that use of the method and apparatus of the present invention does not necessarily preclude its combination for certain purposes with known forms of equipment. For example, the apparatus of FIG. 2 may be incorporated in a scanning tunnelling microscope, so that the STM probe can be used to pick up a molecule and place it on the sample macromolecule already attached in the hole 68, so that the resulting effects can be observed. The probe releases the molecule being carried to the site simply by changing the voltage to the probe. Similarly of course the added molecule may be removed.

We claim:

1. A method of examining samples comprising individual objects of macromolecular size or smaller the method being a non-scanning, non-image-forming method from which measurement of distances is absent and which comprises the steps of:
   (i) bringing a sample into proximity with an instrument element comprising at least one thin film layer having a discontinuity in a known or identifiable location;
   (ii) exciting the instrument element with electromagnetic energy to which the material of said layer is substantially opaque, so as to cause a detectable signal to occur at the discontinuity;
   (iii) causing the sample to move into intimate association with the discontinuity so that the sample and the discontinuity then interact with each other to produce changes in the detectable signal at the discontinuity; and
   (iv) continuing to apply the said energy while detecting said changes, and wherein, the discontinuity consists of an asperity on the film layer, step (iii) comprises bringing the sample into contact, or almost into contact, with the asperity.

2. A method of examining samples comprising individual objects of macromolecular size or smaller the method being a non-scanning, non-image-forming method from which measurement of distances is absent and which comprises the steps of:
   (i) bringing a sample into proximity with an instrument element comprising at least one thin film layer having a discontinuity in a known or identifiable location;
   (ii) exciting the instrument element with electromagnetic radiation to which the material of said layer is substantially opaque, so as to cause a detectable signal to occur at the discontinuity:
   (iii) causing the sample to move into intimate association with the discontinuity so that the sample and the discontinuity then interact with each other to produce changes in the detectable signal at the discontinuity;
   (iv) continuing to apply the said energy while detecting said changes; and,
   (v) applying to the sample and/or the instrument element, at least while step (iv) is being performed, an energy field such as to modify or modulate the behavior of particles and/or structures within the sample.

3. A method according to claim 2, wherein application of the said energy field comprises modulating the energy applied in step (ii).

4. A method according to claim 2, wherein the said energy field is applied as a different form of energy from said electromagnetic radiation.

5. A method of examining samples comprising individual objects of macromolecular size or smaller, being a non-scanning, non-image-forming method, from which measurements of distances is absent and which comprises the steps of:
   (i) bringing a sample into proximity with an instrument element comprising at least one thin film layer of a material substantially opaque optically and having a discontinuity in a known or identifiable location;
   (ii) exciting the instrument element with light so as to cause a detectable optical signal to occur at the discontinuity;
   (iii) causing the sample to move into intimate association with the discontinuity so that the sample and the discontinuity then interact with each other to produce changes in the said signal; and
   (iv) continuing to :apply the said energy while detecting said changes, and further including the step of applying to the sample and/or the instrument element, at least while step (iv) is being performed, a field of acoustic or ultrasonic energy for excitation of the sample such as to modify or modulate the behavior of particles and/or structures within the sample, step (iv) comprising detecting changes in light emitted from the immediate vicinity of the sample and resulting from the said acoustic or ultrasonic excitation.

6. Apparatus for use in performing the method of claim 2 comprising:
   an instrument element comprising at least one thin film layer having a discontinuity in a known or identifiable location; means for causing relative movement between a sample and the discontinuity and for bringing them into intimate association with each other; means for exciting the instrument element with electromagnetic radiation to which the material of said layer is substantially opaque, so as to cause a detectable signal to occur at the discontinuity; and detecting means for detecting said signal and changes therein without scanning or image forming, the apparatus defining means connecting the discontinuity with the detecting means whereby the latter can receive said signal, wherein the discontinuity is an asperity on the film layer.

7. Apparatus for use in performing the method of claim 2, comprising an instrument which includes at least one thin film layer having a discontinuity in a known or identifiable location; means for causing relative movement between a sample and the discontinuity and for bringing them into intimate association with each other; means for applying light to the instrument element whereby to excite the instrument element, so as to cause a detectable signal to occur at the discontinuity; and optical detecting means in line of sight with the discontinuity for detecting said signal and changes therein, without scanning or image forming, wherein the instrument element further includes a substrate on which said at least one film layer is overlaid, said exciting means comprising a light Source, the substrate being translucent for conveying light from said source to the discontinuity.

8. Apparatus for use in performing the method of claim 2, comprising:
an instrument element comprising at least one thin film layer having a discontinuity in a known or identifiable location; means for causing relative movement between a sample and the discontinuity and for bringing them into intimate association with each other; means for exciting the instrument element with electromagnetic radiation to which the material of said layer is substantially opaque, so as to cause a detectable signal to occur at the discontinuity; and detecting means for detecting said signal and changes therein without scanning or image forming, the apparatus defining means connecting the discontinuity with the detecting means whereby the latter can receive said signal, and further including modulating means connected with the instrument element, for applying to a sample at the discontinuity an energy field for modulating said electromagnetic radiation whereby to modify or modulate the behavior of particles and/or structure within the sample.

9. Apparatus for use in performing the method of claim 2, comprising:
an instrument element Comprising at least one thin film layer having a discontinuity in a known or identifiable location; means for causing relative movement between a sample and the discontinuity and for bringing them into intimate association with each other: means for exciting the instrument element with electromagnetic radiation to which the material of said layer is substantially opaque, so as to cause a detectable signal to occur at the discontinuity; and detecting means for detecting said signal and changes therein without scanning or image forming, the apparatus defining means connecting the discontinuity with the detecting means whereby the latter can receive said signal, and further including energy applying means connected with the instrument element, for imposing on the instrument element, and on a sample at the discontinuity, a field of a different form of energy from said electromagnetic radiation, whereby to modify or modulate the behaviour of particles and/or structure within the sample.

* * * * *